United States Patent [19]

Vivat et al.

[11] Patent Number: 4,847,014
[45] Date of Patent: Jul. 11, 1989

[54] NOVEL STEROIDS

[75] Inventors: Michel Vivat, Lagny-sur-Marne; Jean Buendia, Le Perreux-sur-Marne, both of France

[73] Assignee: Roussel Uclaf, Paris, France

[21] Appl. No.: 129,658

[22] Filed: Dec. 7, 1987

[30] Foreign Application Priority Data

Dec. 5, 1986 [FR] France ............................... 86 17050

[51] Int. Cl.$^4$ ........................ C07S 9/00; C07D 221/02
[52] U.S. Cl. .................................. 260/397.1; 540/110
[58] Field of Search ............................ 260/397, 397.1; 540/110

[56] References Cited

U.S. PATENT DOCUMENTS 3,906,095 9/1975 Laurent et al. .

OTHER PUBLICATIONS

Synthesis of 23,23-Difluoro-25-Hydroxyvitamin D3, Taguchi et al., Tet. Lett. (1984), 4933–4936.

*Primary Examiner*—H. M. S. Sneed
*Assistant Examiner*—J. Saba
*Attorney, Agent, or Firm*—Bierman and Muserlian

[57] ABSTRACT

A compound of the formula

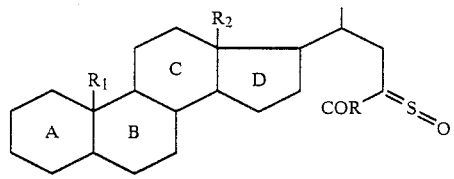

wherein $R_1$ is hydrogen or methyl, $R_2$ is methyl or ethyl, the A,B,C and D rings optionally have one or more double bonds and are optionally substituted with one or more members of the group consisting of halogen protected hydroxy, =O, alkyl and alkoxy of 1 to 4 carbon atoms and alkenyl and alkynyl of 2 to 4 carbon atoms, R is selected from the group consisting of halogen, —OH, alkoxy of 1 to 6 carbon atoms, aralkoxy of 7 to 15 carbon atoms, alkylthio of 1 to 6 carbon atoms, arylthio of 6 to 14 carbon atoms, aralkylthio of 7 to 15 carbon atoms and

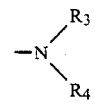

wherein $R_3$ and $R_4$ are individually selected from the group consisting of hydrogen, alkyl of 1 to 6 carbon atoms and aralkyl of 7 to 15 carbon atoms or $R_3$ and $R_4$ together with the nitrogen atom form another heterocycle optionally containing a nitrogen atom or oxygen atom and their preparation and their use to form 20-keto-pregnanes.

8 Claims, No Drawings

NOVEL STEROIDS

STATE OF THE ART

U.S. Pat. No. 4,500,460 and J.A.C.S., Vol. 74, No. 23, p. 5814-5818 are directed to related compounds.

OBJECTS OF THE INVENTION

It is an object of the invention to provide the novel compounds of formula I and a process for their preparation and novel intermediates thereof.

It is another object of the invention to provide a novel method of preparing 20-keto-pregnanes starting from the compounds of formula I.

These and other objects and advantages of the invention will become obvious from the following detailed description.

THE INVENTION

The novel compounds of the invention have the formula

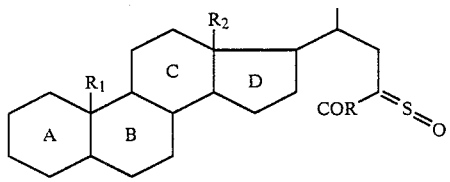

wherein $R_1$ is hydrogen or methyl, $R_2$ is methyl or ethyl, the A, B, C and D rings optionally have one or more double bonds and are optionally substituted with one or more members of the group consisting of halogen protected hydroxy, $=O$ alkyl and alkoxy of 1 to 4 carbon atoms and alkenyl and alkynyl of 2 to 4 carbon atoms, R is selected from the group consisting of halogen, —OH, alkoxy of 1 to 6 carbon atoms, aralkoxy of 7 to 15 carbon atoms, alkylthio of 1 to 6 carbon atoms, arylthio of 6 to 14 carbon atoms, aralkylthio of 7 to 15 carbon atoms and

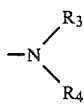

wherein $R_3$ and $R_4$ are individually selected from the group consisting of hydrogen, alkyl of 1 to 6 carbon atoms and aralkyl of 7 to 15 carbon atoms or $R_3$ and $R_4$ together with the nitrogen atom form a heterocycle optionally containing another nitrogen atom or oxygen atom.

When rings A, B, C and D have at least one double bond, they are preferably double bonds in 1(2), 4(5), 5(6) or 9(11) or a system of double bonds conjugated in 3(4) and 5(6) or in 4(5) and 6(7) or an aromatic system of three double bonds 1, 3, 5 or a system of three double bonds 1(2), 4(5), 6(7). However, products not containing a double bond are preferably used.

When rings A, B, C and D are substituted by at least one hydroxy, it is preferably one or more hydroxy functions in the 3, 6, 7, 11 and/or 12 positions. When rings A, B, C and D are substituted by at least one ketone it is preferably to be a ketone in the 3, 7, 11 or 12 position.

When rings A, B, C and D are substituted by at least one halogen, it is preferably fluorine, chlorine or bromine, the 6α- or 9α-position, for example. When rings A, B, C and D are substituted by at least one alkyl, it is preferably methyl or ethyl in the 2, 6, 7, 16α or 16β-position. When rings A, B, C and D are substituted by at least one alkyloxy, it is preferably methoxy of ethoxy in the 3- or 11β-position.

When rings A, B, C and D are substituted by at least one alkenyl, it is preferably vinyl or allyl in 11β-position for example. When rings A, B, C and D are substituted by at least one alkynyl, it is preferably ethynyl in the 11β-position for example.

The hydroxyl may be protected by the usual methods known in the literature such as acetonides, cyclic carbonates, orthoesters, cyclic sulfites, ether formed with tetrahydropyranyl, trityl and benzyl, acyls such as acetyl, succinyl or formyl. The ketone groups may also be protected by the standard protector groups such as ketals, more especially ethylene ketal, thioacetals, hemithioacetals, enol esters, enol acetates, enamines, oximes. However, ketal groups are preferred, and particularly ethylene ketal to protect the ketone groups. When the compounds of formula I contain a 3-ketone, this group is preferentially protected.

R may be halogen such as chlorine or bromine; alkoxy such as, preferably, methoxy or ethoxy, but also propyloxy, isopropyloxy, butyloxy, sec-butyloxy, tert-butyloxy, pentyloxy and hexyloxy; benzyloxy or phenylethyloxy.

$R_3$ and $R_4$ are individually hydrogen or methyl, ethyl, propyl, isopropyl, butyl, sec-butyl, tert-butyl, pentyl, hexyl or benzyl, or $R_3$ and $R_4$ form together with the nitrogen atom to which they are attached morpholine, piperidine or pyrrolidine. R may also be methylthio or ethylthio or alkylthio derived from the alkyl or alkoxy indicated above or phenylthio or benzylthio.

Among the preferred compounds of formula I are those wherein $R_1$ and $R_2$ are methyl and the A, B, C and D rings have an optionally protected 3-hydroxy and optionally, at least one optionally protected hydroxy in the 6, 7, 11 and 12-positions and optionally protected ketone in the 7, 11 and 12-positions and R is halogen, —OH, alkoxy, or

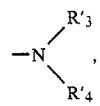

$R_3'$ and $R_4'$ are hydrogen or alkyl of 1 to 4 carbon atoms or together with the nitrogen form piperidino, pyrrolidino or morpholino; those wherein A, B, C and D have an optionally protected 3-hydroxy and optionally at least one optionally protected 12-hydroxy and optionally protected ketone in the 11- or 12-position and R is —OH or chlorine.

Especially preferred compounds of formula I in which A, B, C and D rings have an optionally protected 3-hydroxy and optionally, at least one optionally protected hydroxy in the 6, 7 or 12-positions and optionally protected ketone in the 7, 11 or 12-positions.

In this latter group, there are products containing as a skeleton of rings A, B, C and D products derived from natural or semi-synthetic biliary acids. Examples of these compounds

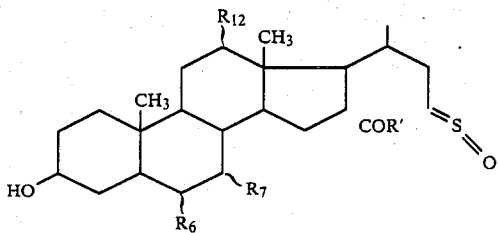

wherein R' is chlorine or hydroxy and $R_6$, $R_7$ and $R_{12}$ have the following significances:

| $R_6$ | $R_7$ | $R_{12}$ |
|---|---|---|
| H | α-OH | α-OH |
| H | β-OH | α-OH |
| H | H | H |
| H | H | α-OH |
| H | α-OH | H |
| α-OH | H | H |
| H | β-OH | H |
| α-OH | α-OH | H |
| β-OH | α-OH | H |
| β-OH | β-OH | H |
| H | α-OH | α-OH |
| H | H | α-OH |

In these products, the hydroxyl can also be protected, particularly the 3-hydroxy. The preferred protector group is acetyl or formyl.

Among the products containing at least one ketone function, the following products are preferred:

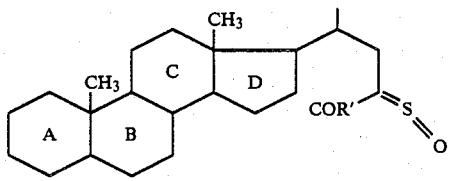

wherein R' is hydroxy and the substituents in the 3, 7, 11 and 12-position have the following defintions
  3 protected ketone
  3α-OH, 7 keto, 12α-OH
  3α-OH 11-keto
  3α-OH, 7α-OH, 12-keto
  3α-OH, 7-keto
  3α-OH, 7β-OH, 12-keto
  3-OH, 11-keto-12-OH
  3-OH-11-keto Of course, the hydroxyl can be protected and the same applies to the ketone in the 7 or 12-position. The preferred protector group for the ketone group is a cyclic or non-cyclic ketal.

Specific preferred products are 3α-formyloxy-23-sulfinyl-5β-cholan-11-one-24-oic acid and 3α-hydroxy-23-sulfinyl-5β-cholan-11-one-24-oic acid.

The process of the invention for the preparation of compounds of formula I comprises reacting a compound of the formula

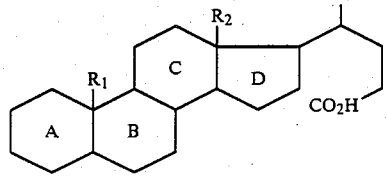

wherein A, B, C, D, $R_1$ and $R_2$ have the above definition first with an agent to form an acid halide, then with a tertiary base, then with thionyl chloride and finally optionally with water, alkanol, aralkanol, primary or secondary amine with the formula

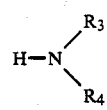

wherein $R_3$ and $R_4$ have the above definition, alkylthiol, arylthiol or aralkylthiol to obtain the corresponding compound of formula I.

In a preferred method of carrying out the above process, the agent for the formation of an acid halide is preferably thionyl chloride, oxalyl chloride or bromide. Among these reagents, thionyl chloride is the preferred reagent. The tertiary base is preferably triethylamine, methylethyl pyridine, pyridine, diazabicyclo-octene, diazabicyclo-nonene, diazabicycloundecane, and more particularly, thriethylamine or pyridine.

The alkanol or aralkanol is preferably methanol, ethanol or benzyl alcohol and the primary or secondary amine is methyl- or ethylamine, diethylamine, morpholine, piperidine and pyrrolidine; of course a corresponding thiol can be used. The alkylthiol, arylthiol or aralkylthiol which can be used is preferably chosen from methanethiol, ethanethiol or thiobenzyl alcohol.

The reactions mentioned above can preferably be carried out in a solvent or a mixture of solvents slightly miscible or not miscible with water such as methylene chloride and chloroform.

The standard blocking or unblocking reactions for the functional groups contained in the A, B, C and D rings can be carried out at the beginning of the synthesis, on products of formula II or on products of formula I. For example, the products of formula I in which the A ring contains a 3-hydroxyl protected by an acyl such as acetyl or formyl can be submitted to a standard saponification reaction to obtain the corresponding product in which the A ring contains a free hydroxyl. The operation is done according to the usual methods by action, for example, of a base such as sodium hydroxide, potassium hydroxide or potassium carbonate in a solvent such as methanol, methylene chloride, water or a mixture of these solvents.

The compounds of formula I are useful as intermediates for the preparation of compounds of the formula

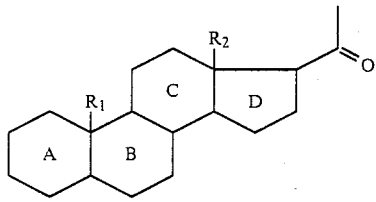

wherein A, B, C, D, R₁ and R₂ have the above definitions by optionally reacting a compound of formula I wherein R is —OH with an agent to form an acid halide to obtain a compound of formula I wherein R is halogen, or treating the product of formula I wherein R has all the above definitions with a halgenation agent and optionally reacting the resulting intermediate wherein R is halogen with a member of the group consisting of water, alkanol, aralkanol, alkylthiol, arylthiol, aralkylthiol and

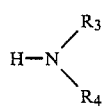

wherein R₃ and R₄ have the above definition to obtain a compound of the formula

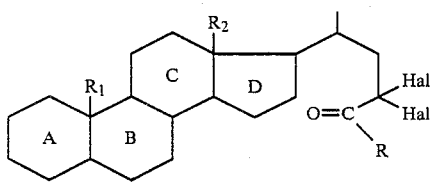

wherein Hal is a halogen and reacting the latter with a dehydrohalogenation agent and then an oxidizing cleavage agent to obtain the corresponding compound of formula IV.

The agent for the optional formation of the acid chloride is one of those discussed above, but preferably is thionyl chloride. The halogenation agent may be a halogen such as bromine or a halogenation agent such as sulfuryl chloride.

When R is halogen, the intermediate product has the formula

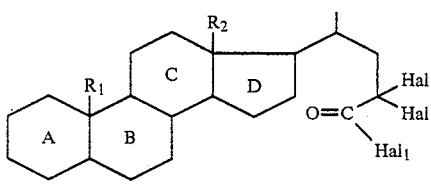

wherein Hal and Hal₁ are halogen and is then optionally reacted with water, alkanol, aralkanol, alkylthiol, arylthiol, aralkylthiol or

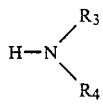

to obtain the corresponding compound of formula II.

The dehydrohydrogenation agent is preferably a strong basic agent such as Triton B,

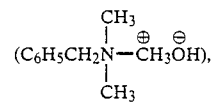

or alkali metal alcoholate such as sodium or potassium ethanolate, potassium tert.-butylate, a sodium or potassium amide. Using a base such as sodium or potassium hydroxide at reflux in an alkanol such as methanol or ethanol or glycol dimethyl ether or a basic resin such as Amberlite may also be used. The oxidizing cleavage agent is preferably chosen from ozone and an oxidizing agent such as ruthenium oxide or manganese oxide.

The action of the dehydrohalogenation reagent on the products of formula III results in a mixture of compounds of the following formulae:

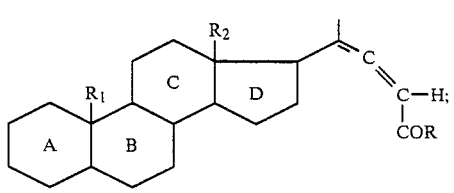

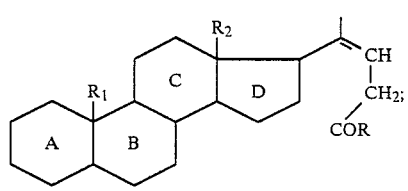

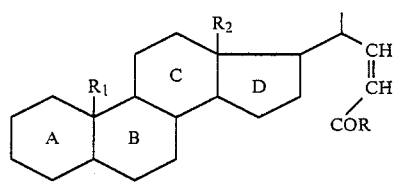

which then, for the products of formulae III₁ and III₂ yield, after oxidizing cleavage, compounds of formula IV. The present process leads in only a slight degree to the product of formula III₃ which is not capable of leading to the final product sought.

Another modification of the process of the invention for the preparation of a compound of formula IV comprises reacting a compound of formula II with an agent for formation of an acid halide, then a tertiary base and finally thionyl chloride to obtain a compound of the formula

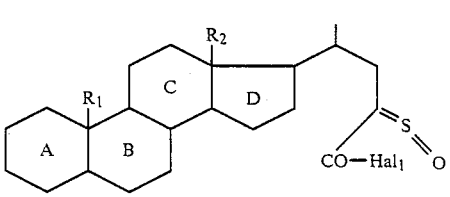

wherein Hal₁ is halogen, reacting the latter with a halogenation agent and optionally reacting the resulting product with a member of the group consisting of water, alkanol, aralkanol, alkylthiol, arylthiol, aralkylthiol and

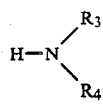

wherein R₃ and R₄ have the above definition to obtain the corresponding compound of formula III and reacting the latter with a dehydrohalogenation agent and then an oxidizing cleavage agent to obtain the corresponding compound of formula IV.

The operating conditions and the reagents employed in the modified process are the same as those employed in the processes above. The advantage of the modified process is that the operation can be done in a single container and without isolating the intermediate product (I_A).

Of course, both in the use of the products with the formula I for the preparation of products with the formula IV and in the process leading from the products with the formula II to the products with the formula IV, the standard blocking and unblocking reactions for the functional groups which the A, B, C and D rings can contain can be carried out either on the starting products of formulae I and II, respectively or on the intermediate products of the synthesis. Especially in the case where the dehydrohalogenation reaction leads to a saponification of the acyl protector group such as acetyl or formyl, the product containing a free hydroxyl can be re-acylated, for example, by acetic anydride in the presence of pyridine. The formation agent of an acid halide is thionyl chloride.

Since the formation of the sulfine group requires the use of thionyl chloride, the preferred reagent for the formation of the acid halide is thionyl chloride in the presence of a tertiary base.

The novel intermediates of the invention are the compounds of the formula

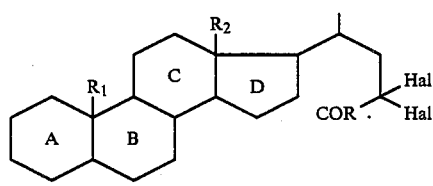

wherein A, B, C, D, R, R₁ and R₂ have the above definitions and Hal is halogen.

The starting products of formula II are known products, for many of the natural products of the biliary acid series, or the products which can be prepared by the usual methods starting from these natural products.

The products of formula IV are products of the progesterone series which possess interesting pharmacological properties and are useful as starting materials for the reconstruction of the deoxycortisone chain:

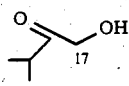

or for other chains in the 17 position.

In the following examples there are described several preferred embodiments to illustrate the invention. However, it should be understood that the invention is not intended to be limited to the specific embodiments.

EXAMPLE 1A

3α-formyloxy-23-sulfinyl-5β-cholan-11-one-24-oic acid 83.7 g of 3α-formyloxy-5β-cholan-11-one-24-oic acid, 840 ml of methylene chloride and 168 ml of pyridine were mixed together and then cooled to +10° C. 32 ml of thionyl chloride were added over 5 minutes allowing the temperature to return to +20° C. and the mixture was stirred at 20° C. for 1 hour. 84 ml of water were added over about 5 minutes at 0° C. and the mixture was stirred at 20° C. for 15 minutes. The reaction mixture was poured into an iced aqueous solution of hydrochloric acid, stirred and decanted, and extraction was carried out with methylene chloride. The extracts were treated with active charcoal, concentrated to dryness by distillation under reduced pressure to obtain 98.5 g of crude product (theory 93 g). Elution with a mixture of chloroform, isopropanol and acetic acid (85/14/1) yielded 3α-formyloxy-23-sulfinyl-5β-cholan-11-one-24-oic acid with an Rf.=0.45.

Analysis: C₂₅H₃₆O₆S: molecular weight=464.60.
Calculated: %C 64.82 %H 7,81 %S 6.90.
Found: 64.8 7.7 7.0.
UV Spectrum (ethanol): Max at 282 nm $E_1^1=157$, $\epsilon=6,400$, or 77% sulfine.
The product was used as is for the following step.

EXAMPLE 1B 23-sulfinyl-5β-cholan-3α-ol-11-one-24-oic acid

The product of Example 1A starting from 4.18 g of 3α-formyloxy-5β-cholin-11-one-24-oic acid was dissolved in a mixture of 15 ml of methanol and 5 ml of methylene chloride. 2 ml of water were added, then potassium carbonate up to saturation. The mixture was held for one hour at 20° C. and was poured into an excess of N hydrochloric acid and extracted with methylene chloride. The extracts were dried on sodium sulfate and distilled to dryness. Crystallization was effected from a methylene chloride-isopropyl ether mixture by concentration to obtain 1.45 g of 23-sulfinyl-5β-cholan-3α-ol-11-one-24-oic acid melting at 221° C. Rf=0.38 (solvent-chloroform, isopropanol, acetic acid (85/14/1).

Analysis: C₂₄H₃₆O₅S; molecular weight=436.59.
Calculated: %C 66.02 %H 8.31 %S 7.34.
Found: 65.8 8.3 7.0.
UV Spectrum: Max at 283 nm: $E_1^1=190$, $\epsilon=8,300$.

EXAMPLE 2

3α-formyloxy-23,23-dichloro-24-diethylamino-5β-cholane-11,24-dione 4.18 g of 3α-formyloxy-5β-cholan-11-one-24-oic acid, 40 ml of methylene chloride and 8 ml of pyridine were mixed together and 1 ml of thionyl chloride was added at 0° C. Then, 2.5 ml of thionyl chloride were added rapidly, and the mixture was stirred at 20° C. for 30 minutes. 11 ml of diethylamine were added at 0° C. and the mixture was stirred at +5° C. for 30 minutes, then allowed to return to 20° C. and was poured into an iced aqueous solution of hydrochloric acid (1.6N). Extraction was carried out with methylene chloride and the extracts were washed with an iced aqueous solution of sodium hydroxide and washed with water. The organic phase was dried and concentrated to dryness under reduced pressure and the residue was chromatographed over silica. Elution with a mixture of cyclohexane and ethyl acetate (80/20) yielded 1.92 g of 3α-formyloxy-23,23-dichloro-24-diethylamino-5β-cholane-11,24-dione.

| IR Spectrum (chloroform) in cm$^{-1}$ | |
|---|---|
| Absence of acid | |
| Presence of formate | 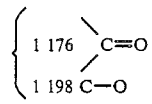 1 176 C=O / 1 198 C—O |
| —C— ‖ O | 1 703 ep. non-conjugated ketone  1 646 tertiary amide |

| NMR Spectrum (CDCl$_3$) in ppm | |
|---|---|
| H of 18 Me | 0.7 |
| H of 19 Me | 1.18 |
| H of 20 Me and CH$_3$ ethyl | 1.1 to 1.24 |
| H of CH$_2$ ethyl doublet | 3.34 to 3.77 |
| H of H$_3$ | 4.8 |
| H of CHO | 8.0 |

EXAMPLE 3

3α-acetoxy-5β-pregnane-11,20-dione (1) Dehydrochloridation 1.7 g of (3α-, 5β-) 23,23-dichloro-N,N-diethyl-3-(formyloxy)-cholan-11-one-24-amide, 17 ml of Triton B, or benzyltrimethyl ammonium hydroxide at 40% in water, and 17 ml of methanol were mixed together, and the mixture was refluxed for 1 hour, then cooled. The reaction mixture was poured into water and extraction was carried out with ethyl acetate. The extracts were concentrated to dryness by distillation under reduced pressure to obtain 1.3 g of the expected crude product.

(2) Acetylation 1.3 g of the crude product obtained above, 2.5 ml of pyridine and 5 ml of acetic anhydride were mixed together and the mixture stood at 20° C. for 16 hours, then was cooled to 0° C. 20 ml of water were added dropwise and the mixture was stirred and decanted. Extraction was carried out with ethyl acetate and the extracts were concentrated to dryness under reduced pressure to obtain the acetylated product which was used as is for the following step.

(3) Ozonolysis

The acetylated product was mixed in 20 ml of methylene chloride and 3 ml of acetic acid and an ozone currnt was passed through this for 30 minutes. The ozonide was destroyed by adding 3 drops of dimethyldisulfide, followed by concentrating to dryness by distilling under reduced pressure. The residue was chromatographed over silica (eluent: cyclohexane-ethyle acetate (90/10) and cyclohexane-ethyl acetate (80/20) to obtain 0.370 g of 3α-acetoxy-5β-pregnane-11,20-dione

| IR Spectrum (chloroform) in cm$^{-1}$ | |
|---|---|
| 21-CH$_3$ | 1,363 |
| \C = 0 (acetate) / | 1,725 |
| \C = 0 (11 keto) / | 1,705 |

EXAMPLE 4

3α-formyloxy-23,23-dibromo-24-diethylaminio-5β-cholane-11,24-dione 418 g of 3α-formyloxy-5β-cholan-11-one-24-oic acid, 400 ml of methylene chloride and 80 ml of pyridine were mixed together under an inert atmosphere. At 0° C., 10 ml of thionyl chloride were added and then immediately 16 ml of bromine and the mixture was stirred at 20° C. for 30 minutes. 108 ml of diethylamine were added at 0° C. and the mixture was stirred at +5° C. for 30 minutes. The reaction mixture was poured into an iced aqueous solution of hydrochloric acid, and extracted with methylene chloride. The extracts were washed with water, then with an iced N aqueous solution of sodium hydroxide, then with water, then dried and treated with active charcoal, and filtered. The filtrates were concentrated to dryness by distillation under reduced pressure to obtain 65.1 g of crude product to which 1 volume of isopropyl ether was added. The precipitate formed was separated, washed and dried to obtain 51.6 g of 3α-formyloxy-23,23-diobromo-24-diethylamino-5β-cholane-11,24-dione melting at 148° C. 1 g of the product was crystallized from a mixture of methylene chloride and petroleum ether (b.p.=60°-80° C.), separated, washed, dried to obtain 840 mg of pure product melting at 162° C.

IR Spectrum (chloroform) in cm$^{-1}$: Absence of acid: presence of formate, ketone (1,703), tertiary amide (1,637)

| NMR Spectrum in ppm | |
|---|---|
| H of 18 Me | 0.7 |
| H of 19 Me | 1.19 |
| H of 20 Me | 1.1–1.18 |
| H$_3$ | 4.9 |
| H of CH$_2$N | 3.4–3.9 |
| H of CH$_0$ | 8.1 |

EXAMPLE 5

3α-formyloxy-23,23-dibromo-24-diethylamino-5β-cholane-11,24-dione 1.4 g of 3α-formyloxy-23-sulfuryl-5β-cholan-11-one-24-oic acid, 14 ml of methylene chloride and 0.97 ml of pyridine were mixed together under an inert atmosphere and at +10° C. 0.24 ml of thionyl chloride were added. The mixture was stirred at 20° C. for 10 minutes, then at 0° C. 1 drop of diterbutyl peroxide was added. Then over 2 minutes, 0.28 ml of bromine were added and the mixture was stirred at 20° C. for 1 hour. Then, 1.32 ml of dethylamine were added at 0° C. with stirring for 15 minutes. The reaction mixture was poured into an iced aqueous solution of hydrochloric acid, and extraction was carried out with methylene chloride. The extracts were washed with water, with a 2N aqueous solution of sodium hydroxide, and with water, then concentrated to dryness by distilling under reduced pressure. Methylene chloride and silica were added to the residue and the mixture was stirred for 30 minutes and filtered. After washing the filtrate and concentrating to dryness by distillation under reduced pressure, 1.4 g of 3α-formyloxy-23,23-dibromo-24-ethylamino-5β-cholane-11,24-dione were obtained. By triturating 500 mg of the product in two volumes of isopropyl ether, 375 mg of purified product were obtained, which was used as is for the following step.

| IR Spectrum (chloroform) in cm$^{-1}$ | |
| --- | --- |
| C = 0 | 1,700–1,720 |
| C = 0 | 1,637 lactam |

EXAMPLE 6

3α-acetoxy-5β-pregnane-11,20-dione (1) Dehydrobromidation 6.6 g of 3α-formyl-23,23-dibromo-24-diethylamino-5β-cholane-11,24-dione, 65 ml of methanol and 65 ml of Triton B or benzyltrimethyl ammonium hydroxide in an aqueous solution titrating 43.3 g/ml were mixed together under an inert atmosphere and maintained at reflux for 1 hour, then cooled in water. The mixture was extracted with methylene chloride and the extracts were washed with a 0.5M aqueous solution of monosodium phosphate, then with water, then dried. Florisil and active charcoal were added and the mixture was stirred, filtered and concentrated to dryness by distillatin under reduced pressure to obtain 4.3 g of product which was used as is for the following step.

(2) Acetylation

The above product 20 ml of pyridine and 12 ml of acetic anhydride were mixed together under an inert atmosphere, and the mixture was stirred at 20° C. for 20 hours. Water was added, and after stirring, the reaction mixture was poured into water and extracted with ethyl acetate. The extracts were washed with water, dried, and concentrated to dryness by distillation under reduced pressure. The pyridine residue was entrained with toluene and the solvents were removed under reduced pressure. The residue was chromatographed [1.85 g of silica, eluting with a mixture of cyclohexane and ethyl acetate (50/50)] to obtain 3.17 g of expected acetylated product which was used as is for the following step.

(3) Ozonization

The acetylated product, 54 ml of dichloroethane and 21 ml of acetic acid were mixed together under an inert atmosphere and the mixture was brought to 0° C. Ozone was bubbled through at +5° C. for 30 minutes and the reaction mixture was poured into water and extracted with methylene chloride. The extracts were washed with water, dried and concentrated to dryness by distillation under reduced pressure. The residue was chromatographed over silica and eluted with a cyclohexane-ethyl acetate mixture (75-25) to obtain 1.44 g of 3α-acetoxy-5β-pregnane-11,20-dione which was crystallized from 4 ml of isopropyl ether to obtain 1.27 g of pure product melting at 128° C.

$[\alpha]_D^{20} = 120.5°$ (c=1% in dimethylformamide).
Analysis: $C_{23}H_{34}O_4$; molecular weight=374.41.
Calculated: %C 73.76 %H 9.25.
Found: 73.7 9.2.
Crystallization from isopropyl ether yielded an 80% yield of product melting at 135° C.

EXAMPLE 7

3α-formyloxy-23,23-dibromo-5β-cholan-11-one-24-oic acid 8 ml of thionyl chloride were added over 5 minutes to a solution at 5° C. of 20.9 g of 3α-formyloxy-5β-cholan-11-one-24-oic acid in 200 ml of methylene chloride and 32 ml of pyridine while allowing the temperature to rise to 20° C. The mixture was stirred for one hour at 20° C., cooled to 10° C. and 8 ml of bromine were added over 5 minutes. The mixture was stirred for one hour at 20° C. and was then poured into a water-ice mixture and decanted. The mixture was re-extracted with methylene chloride, dried on magnesium sulfate, then treated with active charcoal and distilled to dryness. The extracts were taken up in 40 ml of formic acid, heated for 5 minutes at boiling point and then cooled by adding 40 ml of isopropyl ether frozen. After separating, washing with isopropyl ether and drying, 24.6 g of 3α-formyloxy-23,23-dibromo-5β-cholan-11-one-24-oic acid melting at 248° C. and having a Rf=0.4 (chloroform-isopropanol-acetic acid: 85/14/1) were obtained.
Analysis: $C_{25}H_{36}O_5Br_2$; moleculr weight=576.38.
Calculated: %C 52.09 %H 6.3 %Br 27.73.
Found: 52.0 6.3 27.4.

EXAMPLE 8

5β-pregnane-3α-ol-11,20-dione

A suspension of 6 g of 3α-formyloxy-23,23-dibromo-24-diethyl-amino-5β-cholane-11,24-dione of Example 4 in 60 ml of ethanol and 6 ml of 10N sodium hydroxide was refluxed for 16 hours, then cooled to +15° C. and poured into 400 ml of iced water. The mixture was extracted 3 times with 150 ml of ethyl acetate and the extracts were washed with salified water, dried, and evaporated to dryness at 40° C. under reduced pressure. 4.04 g of product were recovered and were dissolved in 200 ml of methylene chloride and 20 ml of methanol and cooled to −65° C. under inert atmosphere. Ozone was bubbled through for 20 minutes, and the mixture was placed under an inert atmosphere. 1.9 g of trimethyl phosphite were added at −65° C. and the mixture was stirred for 15 minutes at −65° C., then allowed to return to 20° C., and evaporated to dryness at 40° C. under reduced pressure. The 6 g of oil obtained were chromatographed over silica and eluted with ethyl acetate to obtain 1.5 g of 5β-pregnane-3α-ol-11,20-dione having been brought to dryness at 40° C. and melting at 168°–170° C.

$[\alpha]_D^{20} = +100.5° \pm 3°$ (c=1% in acetone).

EXAMPLE OF REFERENCE

4-[3α-(acetyloxy)-11,23,24-trioxo-5β-cholan-24-yl)-morpholine

Step A: 3α-acetyloxy-5β-cholan-11—one-24-oic acid
200 g of 5β-cholan-3α-ol-11-one-24-oic acid and 400 ml of acetic anhydride are mixed together and the mixture was heated to 45° C. 2 g of p-toluene sulfonic acid and 20 ml of acetic acid were introduced all at once and the temperature rose to 63° C. in 5 minutes. The mixture was kept at 60° C. for one hour and then was brought down to 55° C. Over about 1 hour, 400 ml of distilled water were added at +55° C., and after cooling to +10° C., the precipitate formed was separated, washed and dried under reduced pressure to obtain 211 g of 3α-acetyloxy-5β-cholan 11—one-24-oic acid melting at 225° C. (purity near to 99%).

106 g of the product obtained were dissolved in methylene chloride, filtered on silica and eluted with a mixture of methylene chloride and ethyl acetate (9/1) to obtain 105 g of purified product melting at 225° C.

| I.R. Spectrum (chloroform in cm$^{-1}$) | | |
|---|---|---|
| OH acid | | |
| 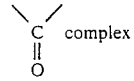 complex | 1720 (ep) | |
| | 1705 (max) | |
| 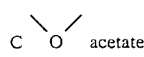 acetate | 1251 | |
| NMR Spectrum (CDCl$_3$) in ppm. | | |
| H of CH$_3$ at position 18 0.62 | H of ACO | 2.03 |
| H of CH$_3$ at position 21 0.88–0.93 | H in position 3 | 4.72 |
| H of CH$_3$ at position 19 1.2 | H of COOH | 8.71 |

Step B: 4-[3α-(acetyloxy)-11,23,24-trioxo-5β-cholan-24-yl)-morpholine

Under an inert atmosphere, 68 g of the product of Step A, 250 ml of methylene chloride and 0.35 ml of N,N-dimethyl-formamide were mixed together and at reflux of the methylene chloride, 12.8 ml of thionyl chloride were added over about 15 minutes. Reflux was maintained for 45 minutes, followed by concentration to dryness by distilling under reduced pressure. 250 ml of methylene chloride were added to the crystallized acid chloride and at −15° c., 12.8 ml of thionyl chloride were added. At −25° C. and over about 90 minutes, a mixture of 46.5 ml of triethylamine and 46.5 ml of methylene chloride were added, and the suspension was stirred for 30 minutes. While maintaining the temperature at −25° C. and over about 30 minutes, a mixture of 35.5 ml of morpholine and 50 ml of methylene chloride were added, with stirring for thirty minutes. Then, over about 10 minutes, 350 ml of water were added, while allowing the temperature to rise towards 0° C. 4.7 ml of acetic acid were added, and at +2° C./+5° C., over about 90 minutes, 49.6 g of potassium permanganate were added. The mixture was diluted during this introduction with 240 ml of water, and stirring was maintained at +2°/+5° C. for one hour. At +5°/+10° C. and over about 30 minutes, 43 g of sodium bisulfite, and simultaneously, a soluton of 12 ml of concentrated sulfuric acid in 150 ml of iced water were added. After decanting, the methylene chloride phase was washed with water and dried, and 5 g of magnesium sulfate and then 60 g of aluminium CBT$_1$ were added under good stirring at 20° C. for 90 minutes. Stirring was maintained for a further 90 minutes at ambient temperature, then after filtering, the filtrate was concentrated to dryness by distilling under reduced pressure. 80 ml of ethyl acetate were added to the residue, followed by concentrating to dryness by distilling under reduced pressure to expel the residual methylene chloride, and 100 ml of ethanol were added to the residue. Solution occurred by stirring at about 40° C. and then the solution was cooled to 0° C., and crystallization was inititated. After standing for 16 hours, 57.6 g of -4-[3α-(acetyloxy)-11,23,24-trioxo-5β-cholan-;B 24-yl)-morpholine melting at 122°–123° C. were obtained. The mother liquors were concentrated to dryness, and a residue of 22 g titrating 83.5% of the expected product were obtained.

| IR Spectrum (chloroform) in cm$^{-1}$. | |
|---|---|
| 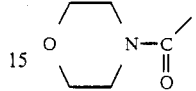 region | 1641 |
|  | 1723 (ep) |
| | 1715 |
| | 1704 |
| NMR Spectrum (CDCL$_3$) in ppm. | |
| H of CH$_3$ in position 18 | 0.67 |
| H of CH$_3$ in position 21 | 0.9–1.0 |
| H of CH$_3$ in position 19 | 1.17 |
| H of ACO | 2.0 |
| H in position 3 | 4.7 |
| H of the morpholine | 3.4–3.8 |

Various modifications of the products and process of the invention may be made without departing from the spirit or scope thereof and it is to be understood that the invention is intended to be limited only as defined in the appended claims.

What we claim is:

1. A compound of the formula

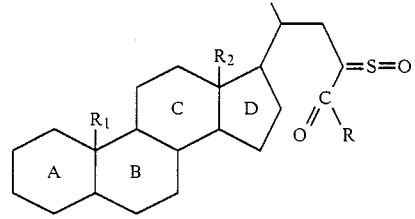

wherein R1 is hydrogen or methyl, R2 is methyl or ethyl, the A, B, C, and D rings are saturated or contain one or more double bonds and their carbon atoms are bondedto one or more members of the group consisting of H, protected hydroxy, =O, haloen, alkyl and alkoxy of 1 to 4 carbon atoms and alkenyl and alkynyl of 2 to 4 carbon atoms, R is selected from the group consisting of halogen, —OH, alkoxy of 1 to 6 carbon atoms, aralkoxy of 7 to 15 carbon atoms, alkylthio of 1 to 6 carbon atoms, arylthio or 6 to 14 carbon atoms, aralkylthio of 7 to 15 carbon atoms and

wherein $R_3$ and $R_4$ are individually selected from the group consisting of hydrogen, alkyl of 1 to 6 carbon atoms and aralkyl of 7 to 15 carbon atoms of $R_3$ and $R_4$ together with the nitrogen atom form a heterocycle or a heterocycle containing an additional nitrogen atom or oxygen atom.

2. A compound of claim 1 wherein R1 and R2 are methyl, R is selected from the group consisting of halogen, —OH, alkoxy of 1 to 4 carbon atoms and

wherein $R_3'$ and $R_4'$ are individually hydrogen or alkyl of 1 to 4 carbon atoms or taken together with the nitrogen atom form a member of the group consisting of piperidino, and morpholino and the A, B, C, and D rings have in the 3-position a hydroxy or protected hydroxy, in the 6, 7, 11 and 12-positions a hydroxy or protected hydroxy, and in the 7,11 and 12 positions a keto or protected keto.

3. A compound of claim 1 wherein R is chlorine or —OH and the A, B, C, and D rings have in the 3-and/or 12-positions a hdyroxy or protected hydroxy, and in the 11-or 12-position may contain a keto or protected keto.

4. A compound of claim 1 which is 3α-formyloxy-23-sulfinyl-5β-cholan-11-one-24-oic acid.

5. A compound of claim 1 which is 23-sulfinyl-5β-cholan-3α-ol-11-one-24-oic acid.

6. A process for the preparation of a compound of claim 1 comprising reacting a compound of the formula

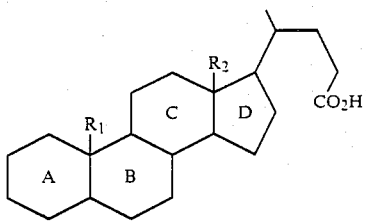

first with an agent for the formation of an acid halide then with a tertiary base and then with thionyl chloride.

7. The process of claim 6 wherein the agent for the formation of the acid halide is thionyl chloride.

8. A process for the preparation of a compound of claim 1 comprising reacting a compound of the formula

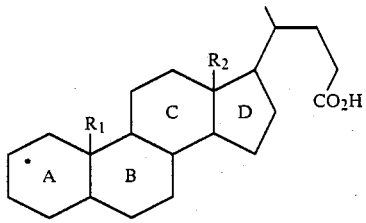

first with an agent for the formation of an acid halide then with a tertiary base and then with thionyl chloride and then with a member selected from the group consisting of water, alkanol, aralkanol, alkylthiol, arylthiol, aralkylthiol and

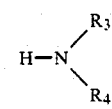

wherein R3 and R4 have the definitions of claim 1 to obtain the corresponding compound of claim 1.

* * * * *